United States Patent [19]

Dolle et al.

[11] Patent Number: 5,677,283
[45] Date of Patent: *Oct. 14, 1997

[54] α-HETEROARYLOXYMETHYL KETONES AS INTERLEUKIN - 1 β CONVERTING ENZYME INHIBITORS

[75] Inventors: Roland E. Dolle, King of Prussia; Jasbir Singh, Gilbertsville, both of Pa.; David A. Whipple, New London, Conn.; Catherine Prouty, Doylestown, Pa.; Prasad V. Chaturvedula, Cheshire, Conn.; Stanley J. Schmidt, Chester Springs, Pa.; Mohamed M. A. Awad, Westerly, R.I.; Denton W. Hoyer, Exton; Tina Morgan Ross, Audubon, both of Pa.

[73] Assignee: Sanofi, Paris, France

[*] Notice: The term of this patent shall not extend beyond the expiration date of Pat. No. 5,585,357.

[21] Appl. No.: 732,173

[22] Filed: Oct. 16, 1996

Related U.S. Application Data

[63] Continuation of Ser. No. 593,773, Jan. 29, 1996, Pat. No. 5,585,357, which is a continuation-in-part of Ser. No. 237,920, Apr. 29, 1994, abandoned, which is a continuation-in-part of Ser. No. 71,623, Jun. 3, 1993, abandoned.

[51] Int. Cl.$^6$ .................. A61K 38/00; A61K 31/415; C07K 5/00; C07D 231/04
[52] U.S. Cl. .................. 514/18; 514/17; 514/19; 514/402; 530/330; 530/332; 548/370.1
[58] Field of Search .................. 514/18, 17, 19, 514/407; 530/330, 332; 548/370.1

[56] References Cited

U.S. PATENT DOCUMENTS 5,055,451  10/1991  Krantz et al. .
5,434,248  7/1995  Chapman et al. .

FOREIGN PATENT DOCUMENTS 0 519 748 A2  6/1992  European Pat. Off. .
WO 91/15577  10/1991  WIPO .

*Primary Examiner*—Marian C. Kmode
*Assistant Examiner*—Benet Prickril
*Attorney, Agent, or Firm*—William J. Davis; Imre Balogh

[57] ABSTRACT

Compounds which Inhibit interleukin-1β protease activity, pharmaceutical compositions containing the compounds and methods using the compounds are provided. The compounds have the formula $$R_1-(AA)_n-N-\underset{\underset{H}{|}}{\overset{\overset{H}{|}}{C}}-\underset{\underset{O}{\|}}{\overset{\overset{CH_2-C-OH}{|}}{C}}-CH_2-O-\underset{\underset{R_8}{|}}{\overset{R_{10} \quad R_9}{\diagup\diagdown N}}$$

wherein n is 0–2; each AA is Independently L-valine or L-alanine;

R$_1$ is selected from the group consisting of N-[4(N,N-dimethylaminomethyl)]benzoyl, N-benzoyloxycarbonyl, N-methyl-N-[4-(pyridyl)methyl], N-[4-(pyddyl)methyl]carbonyl, N-3-(piperidinopropionyl), N-[4-(morpholinoethoxy)benzoyl, N-2-(quinuclidinyl)carbonyl, N-(3-pyridyl)methoxy carbonyl, N-(2-pyddyl)methoxy carbonyl, N-methyl-N-benzyl carbonyl, N-methyl-N-[2-(4-pyridyl)ethyl]carbonyl, and N-(N-phenylpiperazino) carbonyl; and R$_8$, R$_9$ and R$_{10}$ are as defined below.

3 Claims, No Drawings

α-HETEROARYLOXYMETHYL KETONES AS INTERLEUKIN - 1 β CONVERTING ENZYME INHIBITORS

This application is a continuation of application Ser. No. 08/593,773 filed Jan. 29, 1996, now U.S. Pat. No. 5,585,357 which is a continuation-in-part of application Ser. No. 08/237,920 filed on Apr. 29, 1994, now abandoned, which is a continuation-in-part of Ser. No. 08/071,623 filed on Jun. 3, 1993, now abandoned.

BACKGROUND OF THE INVENTION

1. Field of the Invention

This invention relates to a series of novel amino acid, di- and polypeptide analogs which exhibit selective inhibition of interleukin-1β-converting enzyme, to compositions containing the novel amino acid analogs and methods for therapeutic utility. More particularly, the interleukin-1β-converting enzyme inhibitors described in this invention comprise novel α-substituted methyl ketones which possess particular utility in the treatment of inflammatory and immune-based diseases of lung, central nervous system, and connective tissues.

2. Reported Developments

Interleukin-1 β protease (also known as interleukin-1 β-converting enzyme or ICE) is the enzyme responsible for processing of the biologically inactive 31 kD precursor IL-1 β to the biologically active 17 kD form (Kostura, M. J.; Tocci, M. J.; Limjuco, G.; Chin, J.; Cameron, P.; Hillman, A. G.; Chartrain, N. A.; Schmidt, J. A. *Proc. Nat. Acad. Sci.*, 1989, 86, 5227–5231 and Black, R. A.; Kronheim, S. R.; Sleath, P. R. FEBS Let., 1989, 247, 386–391). In addition to acting as one of the body's early responses to injury and infection, IL-1 β has also been proposed to act as a mediator of a wide variety of diseases, including rheumatoid arthritis, osteoarthritis, inflammatory bowel disease, sepsis, and acute and chronic myelogenous leukemia (Dinarello, C. A.; Wolff, S. M., *New Engl. J. Med.*, 1993, 328, 106). The naturally occurring IL-1 β receptor antagonist has been used to demonstrate the intermediacy of IL-1 β in a number of human diseases and animal models (Hannum, C. H.; Wilcox, C. J.; Arend, W. P.; Joslin, G. G.; Dripps, D. J.; Heimdal, P. L.; Armes, L. G.; Sommer, A.; Eisenberg, S. P.; Thompson, R. C., *Nature*, 1990, 343, 336–340; Eisenberg, S. P.; Evans, R. J.; Arerid, W. P.; Verderber, E.; Brewer, M. T.; Hannum, C. H.; Thompson, R. C., *Nature* 1990, 343, 341–346; Ohlsson, K.; Bjork, P.; Bergenfeldt, M.; Hageman, R.; Thompson, R. C., *Nature*, 1990, 348, 550–552; and Wakabayashi, G., GASEB, 1991, 338–343). The specific role of IL-1 p in inflammation and immunomodulation is supported by the recent observation that the cowpox virus employs an inhibitor of ICE to suppress the inflammatory response of its host (Ray, C. A. et al, *Cell*, 1992, 69, 597–604).

The present invention also relates to the modulation of processing of IL-1 β for the treatment of rheumatoid arthritis. Levels of IL-1 β are known to be elevated in the syncvial fluid of patients with the disease. Additionally, IL-1β stimulates the synthesis of enzymes believed to be involved in inflammation, such as collagenase and PLA$_2$, and produces joint destruction which is very similar to rheumatoid arthritis following intra-articular injection in animals.

A limited number of peptidyl methyl ketone analogs constitute a well-known class of compounds having cysteine protease (papain, cathepsin B) inhibitory activity. These peptidyl methyl ketone analogs have been reviewed by D. Rich in Chapter 4 of "Proteinase Inhibitors", Barrett, A. J. and Salvensen, G., eds., Elsevier, 1986. More recently, a-aryloxy and a-arylacyloxy methyl ketones have also been described as inhibitors of cysteine protease (Krantz, A. et al, Biochemistry, 30, p. 4678–4687, 1991).

These peptide analogs, however, are essentially devoid of potency and selectivity in inhibiting ICE.

An effective therapy has yet to be developed for the treatment of IL-1 β mediated inflammatory diseases. Consequently, there is a need for therapeutic agents effective in the treatment and prevention of these diseases.

SUMMARY OF THE INVENTION

According to the present invention, there is provided a compound of the formula (I) and a pharmaceutically acceptable salt thereof:

wherein:

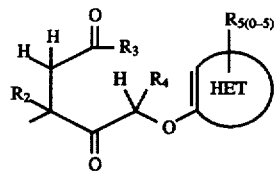

and when R$_3$ is OH, then Y can also be

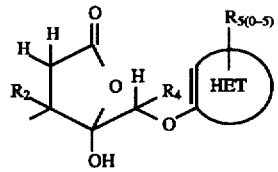

R$_2$ is H or deuterium;

R$_3$ is OH, OR$_6$, NR$_6$OR$_7$ or NR$_6$R$_7$, where R$_6$ and R$_7$ are independently H, alkyl, aralkyl, heteroaralkyl, aryl or heteroaryl;

R$_4$ is H or alkyl;

R$_5$ is H, alkyl, alkenyl, aryl, heteroaryl, aralkyl, heteroaralkyl, aralkenyl, heteroaralkenyl, hydroxy, alkoxy, 2-(alkyoxy)ethoxy, 2-(alkyoxy)aminoethyl and 2-(alkyoxy)-N-alkylaminoethyl, aralkoxy, heteroaralkoxy, alkylacyloxy, aralkylacyloxy, heteroaralkylasyloxy, aracyloxy, heteroaracyloxy, aryloxyalkylacyloxy, heteroaryloxyalkylacyloxy, alkylacyl, aralkylacyl, heteroaralkylacyl, alkylacylamino, aralkylacylamino, heteroaralkylacylamino, aracylamino, heteroaracylamino, aryloxyalkylacylamino, heteroaryloxyalkylacylamino, alkyloxyalkylacylamino, alkoxyacylamino, aralkoxyacylamino, heteroaralkoxyacylamino, aracyl, heteroaracyl, aryloxyalkylacyl, heteroaryloxyalkylacyl, halo, haloalkyl, guanidino, mono- and di-alkylguanidino, mono- and di-aralkylguanidino, mono- and di-heteroaralkylguanidino, alkylacylguanidino, aralkylacylguanidino, heteroaralkylguanidino, aracylguanidino, heteroarylguanidino, amidino, mono- and di-alkylamidino, mono- and diaralkylamidino, mono- and di-heteroaralkylamidino, amino, mono- and dialkylamino, mono- and di-aralkylamino, mono- and di-heteroaralkylamino, carboxy, alkylcarboxy, carbalkoxy, carbalalkoxy, carbheteroaralkoxy, carbalkoxyalkenyl, carboxamido, mono- and dialkylcarboxamido, mono- and diarcarboxamido, mono and di-heteroarcarboxamido, mono- and di-aralkylcarboxamido, mono- and di-heteroaralkylcarboxamido, thio, alkylthio, arylthio, heteroarylthio, aralkylthio, heteroaralkylthio, sulfonamido, mono- and di-alkylsulfonamido, mono- and di-aralkylsulfonamido, mono- and di-heteroaralkylsulfonamido, morpholinosulfonamido, alkylsulfonyl, aralkylsulfonyl, heteroaralkylsulfonyl, arylsulfonyl, heteroarylsulfonyl, nitro, cyano, N-morpholinoaikyl, N-morpholinoalkoxy, N-morpholinoaralkyl, N-morpholinoaralkoxy, N-morpholinoheteroaralkyl, N-morpholinoheteroaralkoxy, N-mono and N,N-dialkylaminoalkyl and N-mono- and N,N-dialkylaminoethoxy, quinuclidinylamino, quinuclidinyloxy, quinuclidinocarbonyl or ureido;

HET is a heteroaryl;

AA is independently selected from the group consisting of (a) and (b) where group (a) is defined as an amino acid of formula II:

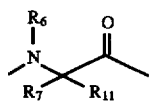
(II)

where $R_6$ and $R_7$ are defined as above and $R_{11}$ is $(CR_6R_7)_{0-6}$—$R_{12}$ where $R_{12}$ is designated as either an aryl, heteroaryl or a radical optionally selected from $R_5$ wherein $R_5, R_6, R_7$ are defined previously;

and group (b) is selected from the group consisting of:

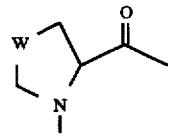
(1)

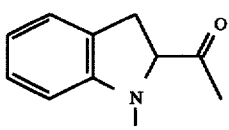
(2)

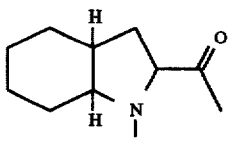
(3)

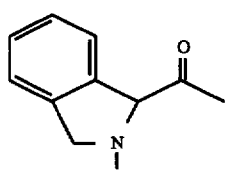
(4)

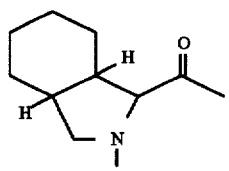
(5)

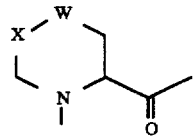
(6)

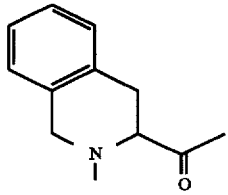
(7)

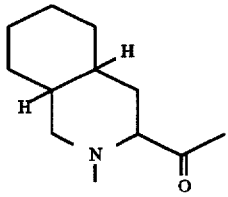
(8)

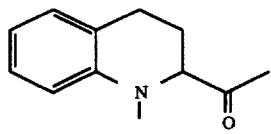
(9)

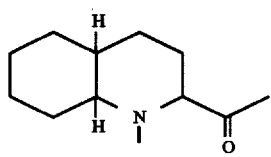
(10)

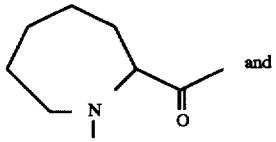
(11) and

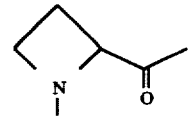
(12)

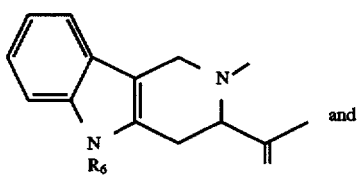
(13) and

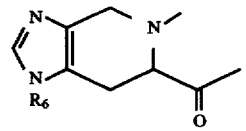
(14)

where W and X are optionally $CH_2$, O, S, or $NR_6$; and $R_1$ is $R_{12}$—CO— or $R_{12}SO_2$—,
where $R_{12}$ is as previously defined.

Heteroaryl is defined as an unsubstituted or an optionally substituted mon- or bicyclio ring system of about 5 to about 12 carbon atoms and where each monocyclic ring may possess from 0 to about 4 heteroatoms, and each bicyclic ring may possess about 0 to about 5 heteroatoms selected form N, O, and S provided said heteroatoms are not vicinal oxygen and/or sulfur atoms and were the substituents, numbering from 0 to about 5 may be located at any appropriate position of the ring system and are described by $R_5$.

Examples of such mono- and bicyclic ring systems which are by no means meant to limit the scope of this invention, include benzofuran, benzothiophene, indole, benzopyrazole, coumarin, isoquinoline, pyrrole, thiophene, furan, thiazole, imidazole, pyrazole, triazole, quinoline, pyrollidenone, pyrimidine, pyridine, pyridone, pyrazine, pyridazine, isothiazole, isoxazole and tetrazole.

A preferred embodiment of this invention is where HET is the pyrazole of formula III:

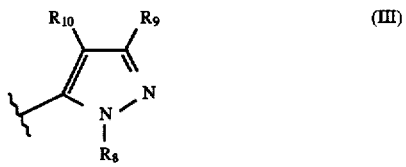

wherein $R_8$, $R_9$ and $R_{10}$ are independently aryl, heteroaryl, or a radical optionally selected from $R_5$; and where $R_9$ and $R_{10}$ taken together may be aryl, heteroaryl, cyclopentyl, cyclohexyl, cycloheptyl or cyclooctyl.

As used herein, the term pharmaceutically acceptable salts include the acid and base addition salts.

The term acid addition salts refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

As employed above and throughout the disclosure, the following terms, unless otherwise indicated, shall be understood to have the following meanings:

"Alkyl" is defined as a saturated aliphatic hydrocarbon which may be either straight- or branched-chain or cyclic. Preferred groups have no more than about 12 carbon atoms and may be methyl, ethyl and structural isomers of propyl, butyl, pentyl, hexyl, heptyl, octyl, nonyl, decyl, undecyl, dodecyl, cyclopropyl, cyclobutyl, cyclopentyl, cyclohexyl, cycloheptyl and cyclooctyl.

"Aryl" is defined as a phenyl or naphthyl or a substituted phenyl and a substituted naphthyl ring wherein one or more of the hydrogens has been replaced by the same or different substituents aS selected from $R_5$.

"Alkoxy" refers to an alkyl-O-group. For example, methoxy or ethoxy.

"Aryloxy" refers to an aryl-O-group. For example, phenoxy.

"Heteroxy" refers to a hetero-O-group. For example, 4-pyridyloxy.

"Aralkyl" refers to an alkyl group substituted by an aryl radical. For example, benzyl.

"Heteroaralkyl" refers to an alkyl group substituted by a heteroaryl radical. For example, (4-pyridyl)methyl.

"Alkenyl" is defined as an unsaturated aliphatic hydrocarbon which may be either straight- or branched-chain of cyclic. Preferred groups have no more than about 12 carbon atoms and no fewer than 2 carbon atoms and contain from one to up to about 6 double bonds. Examples of alkenyl groups include ethenyl, propenyl, 1-hexenyl, 1-3-hexdienyl, 2-methyl-2-butenyl, 2-methyl-3-pentenyl, cyclopentenyl, cyclohexenyl and cyclobutenyl.

"Alkylacyl" refers to an alkyl-C(O)-group. For example, acetyl or propionyl.

"Alkylacyloxy" refers to an alkyl-C(O)O-group. For example, an acetoxy group.

"Alkylacylamino" means alkyl-C(O)-$NR_7$ where $R_7$ has been defined previously.

"Alkylacylguanidino" means alkyl-C(O)$NR_6C(NR_7)$NH— where $R_6$ and $R_7$ have been defined previously.

"Ureido" refers to an $R_6R_7$N—C(O)—N—$R_6$-group where $R_6$ and $R_7$ are described previously.

"Haloalkyl" is defined as a saturated aliphatic hydrocarbon of 1–12 carbon atoms which may be either straight- or branched-chain or cyclic and where one or more of the hydrogen atoms is replaced with halogen. Preferred haloalkyl groups include trifluoromethyl and pentafluoroethyl.

"Halo" means bromo, chloro and fluoro.

The present invention also concerns the pharmaceutical composition and method of treatment of IL-1 β protease mediated disease states or disorders in a mammal in need of such treatment comprising the administration of IL-1β protease inhibitors of formula (I) as the active agent. These disease states and disorders include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based disease, such as hypersensitivity; autoimmune diseases, such as multiple sclerosis; bone diseases; and certain tumors.

In the practice of this invention an effective amount of a compound of the invention or a pharmaceutical composition thereof is administered to the subject in need of, or desiring, such treatment. These compounds or compositions may be administered by any of a variety of routes depending upon the specific end use, including orally, parenterally (including subcutaneous, intraarticular, intramuscular and intravenous administration), rectally, buccally (including sublingually), transdermally or intranasally. The most suitable mute in any given case will depend upon the use, the particular active ingredient, and the subject involved. The compound or composition may also be administered by means of controlled-release, depot implant or injectable formulations as described more fully herein.

In general, for the uses as described in the instant invention, it is expedient to administer the active ingredient in amounts between about 0.1 and 100 mg/kg body weight, most preferably from about 0.1 to 30 mg/kg body weight for human therapy, the active ingredient will be administered preferably in the range of from about 0.1 to about 20–50 mg/kg/day. This administration may be accomplished by a single administration, by distribution over several applications or by slow release in order to achieve the most effective results. When administered as a single dose, administration will most preferably be in the range of from about 0.1 to mg/kg to about 10 mg/kg.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

A further aspect of the present invention relates to pharmaceutical compositions comprising as an active ingredient a compound of the present invention in admixture with a pharmaceutically acceptable, non-toxic carrier. As mentioned above, such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

When administered orally (or rectally) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, aginates, tragacanth, gelatin, syrup, methylcellulose, polyoxyethylene sorbitar monolaurate, methyl hydroxybenzoate, propyl hydroxybenzoate, talc, and magnesium stearate.

The compositions may be prepared by any of the methods well-known in the pharmaceutical art, for example as described in *Remington's Pharmaceutical Sciences*, 17th edition, Mack Publishing Company, Easton, Pa., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Examples of vehicles for parenteral administration include water, aqueous vehicles such as saline, Ringer's solution, dextrose solution, and Hank's solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. For oral administration, the formula can be enhanced by the addition of bile salts and also by the addition of acylcarnitines (*Am. J. Physiol.* 251:332 (1986)). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, ethocholic acid, desoxycholic acid, chenodesoxycholic acid, dehydrocholic acid, glycodeoxycholic acid, and the like (See, B. H. Vickery, "LHRH and its Analogs-Contraception and Therapeutic Applications", Pt. 2, B. H. Vickery and J. S. Nester, Eds., MTP Press, Lancaster, UK, 1987).

DETAILED DESCRIPTION OF THE INVENTION

The compounds of this invention are prepared by one of two related general synthetic methods as described in Schemes 1 and 2. Referring to Scheme I, the first step of the method involves the synthesis of Z-protected amino acid bromomethyl ketones (formula 2), where the "Z-group" refers to the "benzyloxycarbonyl group". Methods for the preparation of various Z-protected aspartic acids and aspartic acid-containing peptides (formula 1) which are used as the starting materials for the synthesis of bromomethyl ketones (formula 2) are well established in the art. (See, for example, "The Peptides", E. Gross and J. Meienhofer, Eds. Academic Press, Orlando, Fl., Vol. 1–3, 1979.) The Z-protected amino acids, dipeptides, and polypeptides (formula 1), which in some cases are commercially available, are then converted to the aspartic acid-containing bromoketones (formula 2) by way of hydrobromination of a diazomethyl ketone intermediate. This is accomplished by methods described in Shaw, E. and Ruscica, J.; *J. Biol. Chem.*, 1968, 243, 6312 and Green, E. D. J. and Shaw, E.; *J. Biol. Chem.*, 1981, 256, 1923.

The t-butyl ester bromoketone (formula 2) is reacted with a variety of pyrazolones. This is conducted by exposing the bromomethyl ketone to an excess of the pyrazolone in a DMF containing sodium or potassium hydride or potassium fluoride. The reaction can be conveniently monitored by thin layer chromatography (TLC) and once the TLC indicates that the displacement of the bromide with the pyrazolone is completed, the product is isolated using standard procedures. The desired aspartic acid-pyrazolylmethyl ketone mono-t-butyl ester (formula 3) may be purified by conventional methods including recrystallization and silica gel column chromatography.

SCHEME 1

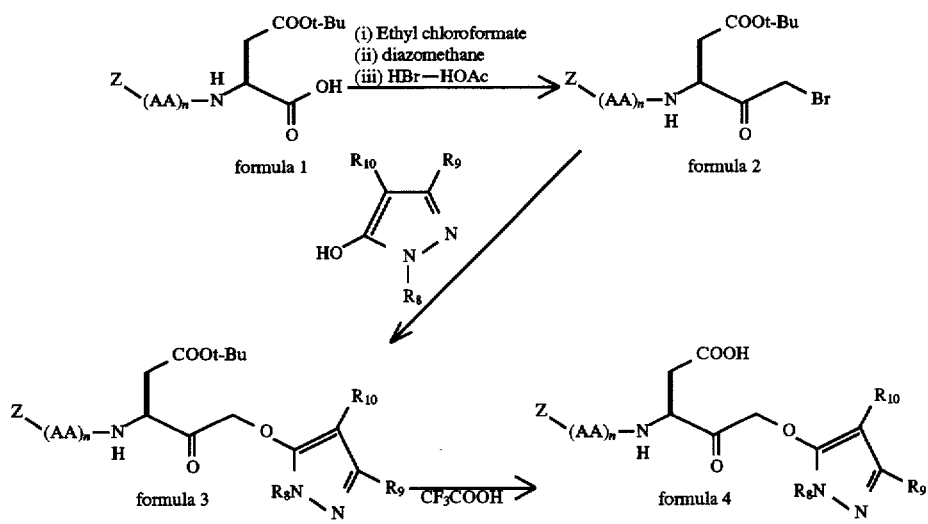

SCHEME 2

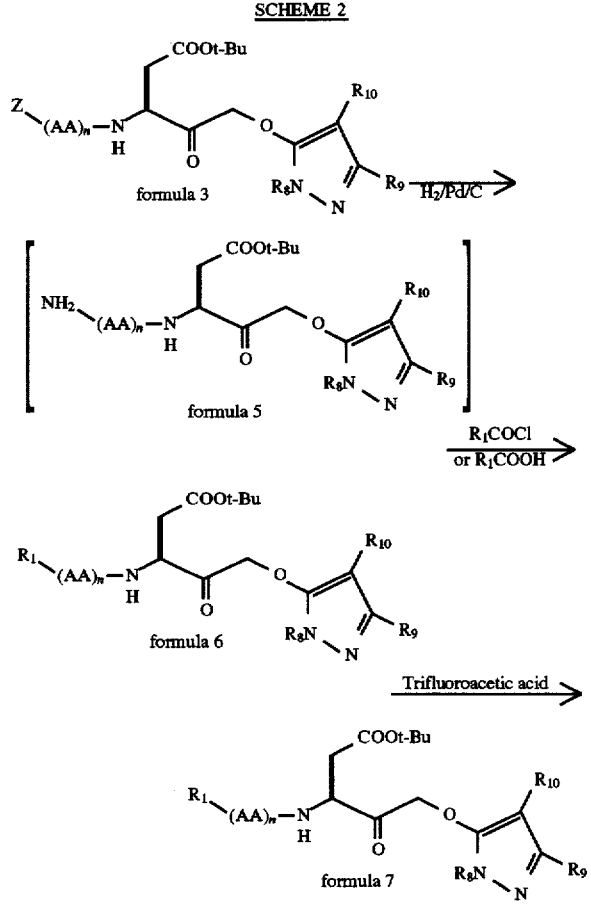

wherein

AA, $R_1$, $R_8$, $R_9$, $R_{10}$ and n are as defined in formula (I) and Z is defined as the benzyloxycarbonyl group.

The remaining synthetic transformation to generate the ICE inhibitors is hydrolysis of the t-butyl ester function. This is conducted by exposing the ester to a 25% solution of trifluoroacetic acid in methyl chloride at 25° .C. The de-esterification is usually complete within 3 h and the removal of the volatile TFA and solvent affords the aspartic acid derivative (formula 4). The yield of the reaction is quantitative in most instances, providing the t-butyl ester starting material is of high purity. Purification, if required, can be performed by recrystallization or chromatographic techniques which are well known to those skilled in the art. A solution of 3 molar anhydrous HCl in ethyl acetate may be used in place of TFA-methylene chloride solution with equal efficiency.

In scheme 2, the synthesis of pyrazolyloxymethyl ketones, which possess an N-terminal group, other than the Z- group are described. The aspartic acid derivatives of formula 3 are the starting material for the synthesis of these compounds. The Z- group is removed to generate an N-terminal amine (formula 5) under hydrogenolytic conditions. The reagents and conditions used to carry out the hydrogenation reaction are hydrogen gas, ambient temperature and pressure, 5%-Pd/C as the catalyst in an alcoholic solvent (ethanol), optionally containing 2 equivalents of hydrochloric acid.

The N-terminal amine is then condenced with carboxylic acid chloride or a mixed arthydride (The Practice of Peptide Synthesis: M Bodanszky, Springer-Verlag, NY,1984) to yield an iamide (formula 6). Lastly, the t-butyl ester is removed with trifluoroacetic acid to afford the aspartic acid derivative (formula 7).

Compounds of formulas 4 and 7 may exist as a cyclic hemiketal (where the carboxylate oxygen adds intramolecularly to the ketone carbonyl) and such structures are considered within the scope of this invention.

The pyrazolones used in the reaction with the bromomethyl ketones can be either purchased from commercial sources or synthesized by adopting known procedures including those described in (1) Hansel, W., Justus Liebigs Ann, Chem., 1976, 1380–1394; (2) Knorr, L., Justus Liebigs Ann. Chem., 1987, 238, 137; (3) Watanabe, Y. et al, Chem. Pharm. Bull. (Japan), 1990, 38, 2726; (4) Grillot, G. F. et al, J. Org. Chem,, 1958, 23, 119. Their synthesis is readily deduced by those skilled in the art of organic synthesis.

The following examples will further illustrate the compounds of the present invention.

EXAMPLE 1

N-4-(N,N-Dimethylaminomethyl)]benzoyl-L-valine-L-aspartic acid 5-(1-phenyl-3-trifluoromethyl) pyrazoyloxymethyl ketone Part A N-Benzyloxycarbonyl-L-valine-L-aspartic acid bromomethyl ketone p-tert butyl ester (1.16 mmol) was dissolved in 2 mL of DMF containing 1-phenyl-3-trifluoromethyl-5-pyrazolone (1.4 mmol) and powdered anhydrous KF (1.6 mmol). The reaction mixture was stirred under $N_2$ for 16. hrs. The mixture was diluted with water (30 mL), extracted with ether (3×20 mL), and the organic layer was washed with 0.1N NaOH (3×10 mL) followed by brine. The ether solution was dried over magnesium sulfate and concentrated in vacuo to afford (85%) of the p-tert-butyl ester (formula 3) as a brown solid.

Part B: N-Benzyloxycarbonyl-L-valine-L-aspartic acid 5-(1-phenyl-3-trifluoromethyl)pyrazoyloxymethyl ketone p-tert-butyl ester (2 mmol; Part A above) was dissolved in absolute ethanol (100 mL) containing 2 equiv. of 6N aqueous HCl (4 mmol) and 10% palladium on carbon. The reaction mixture was stirred under an ambient atmosphere of $H_2$ gas for about 1 hr. The solution was filtered and the solvent was removed in vacuo to give the corresponding HCl-salt (formula 6) which was used immediately in the subsequent reaction.

Part C: The HCl-salt obtained in Part B above was dissolved in $CH_2Cl_2$ (10 mL), cooled to −20° C. and N-[4-(N,N-dimethylaminomethyl)]benzoyl chloride (4 mmol) was added followed by the addition of 10 mg of dimethylamino pyridine (DMAP) and N-methylmorpholine (5 mmol). The reaction mixture was stirred for 2 hrs at 25° C. The solvent was removed in vacuo and the residue was dissolved in EtOAc (10 mL) which was then washed with water, 0.01N aqueous HCl, saturated $NaHCO_3$, brine and dried over $MgSO_4$. The EtOAC was removed in vacuo and the residue was chromatographed on silica gel ($CH_2Cl_2$-MeOH) to obtain N-(4-(N,N-dmethylaminomethyl)benzoyl-L-valine-L-aspartic acid (5-(1-phenyl-3-trifluoromethyl) pyrazoyloxymethyl ketone β-tert-butyl ester (formula 7) in 50% yield.

Part D: The 13-tert-butyl ester obtained in Part C above (1 mmol) was dissolved in 25% trifluoroacetic acid—75% $CH_2Cl_2$ and the solution was stirred for 2 hrs at 25° C. The solvent was removed in vacuo and the residue was triturated with ether. The white solid was collected and dried to give the title compound in 100% yield. Mass spectrum: m/z 618 (M+H).

The 4-(N,N-dimethylaminomethyl) benzoyl chloride was prepared by reacting the acid with excess oxalyl chloride for 1 hr at 25° C. The 4-(N,N-dimethylaminomethyl) benzoic acid was in turn prepared from methyl 4-aminomethylbenzoate via reductive alkylation ($CH_2O$, $Na(OAc)_3BH$ as in *J. Org. Chem.*, 1972, 37, 1673) followed by hydrolysis using 10% aqueous NaOH.

Following the procedure described in Schemes 1 and 2 and by analogy with Example 1, the following compounds were prepared.

EXAMPLE 2

N-Benzyloxycarbonyl-L-aspartic acid 5-(1,3-dimethyl)pyrazolyloxymethyl ketone

Mass spectrum: m/z=376 (M+H)

EXAMPLE 3

N-Benzyloxycarbonyl-L-aspartic acid 5-(1-phenyl-3-trifluoromethyl)pyrazolyloxy methyl ketone.

Mass spectrum: m/z=492 (M+H)

EXAMPLE 4

N-Benzyloxycarbonyl-L-aspartic acid 5-(1-(p-fluorophenyl)-3-methyl)pyrazolyloxymethyl ketone.

Mass spectrum: m/z=456 (M+H)

EXAMPLE 5

N-Benzyloxycarbonyl-L-aspartic acid 5-(1-(p-nitrophenyl)-3-methyl)pyrazolyloxymethyl ketone.

Anal. Calcd. for $C_{23}H_{22}N_4O_8 \cdot CF_3CO_2H$: C, 50.34; H, 3.89; N, 9.39. Found: C, 50.48; H, 4.02; N, 9.33

EXAMPLE 6

N-Benzyloxycarbonyl-L-aspartic acid 5-(1-(p-methoxyphenyl)-3-methyl)pyrazolyloxymethyl ketone.

Anal. Calcd. for $C_{24}H_{25}N_3O_7 \cdot 1.25\ CF_3CO_2H$: C, 52.18; H, 4.34; N, 6.89. Found: C, 51.94; H, 4.30; N, 6.71

EXAMPLE 7

N-Benzyloxycarbonyl-L-aspartic acid 5-(1-(p-chlorophenyl)-3-methyl)pyrazolyloxymethyl ketone.

Mass spectrum: m/z=472 (M+H)

EXAMPLE 8

N-Benzyloxycarbonyl-L-valine-L-alanine-L-aspartic acid 5-(1-.phenyl-3-methyl)-pyrazolyloxymethyl ketone.

Mass spectrum: m/z=608 (M+H)

EXAMPLE 9

N-Benzyloxycarbonyl-L-aspartic acid 5-(1-phenyl-3-methyl)pyrazolyloxymethyl ketone.

Mass spectrum: m/z=438 (M+H).

EXAMPLE 10

N-Benzyloxycarbonyl-L-aspartic acid 5-(1-(m-chlorophenyl)-3-methyl pyrazolyloxymethyl ketone.

Anal. Calcd. for $C_{23}H_{22}ClN_3O_6 \cdot 0.9\ CF_3CO_2H$: C, 51.85; H, 4.02; N, 7.31. Found: C, 52.08; H, 4.24; N, 6.98

EXAMPLE 11

N-Benzyloxycarbonyl-L-aspartic acid 5-(1-benzyl-3-trifluoromethyl)pyrazolyloxy methyl ketone.

Mass spectrum: m/z=506 (M+H)

EXAMPLE 12

N-Benzyloxycarbonyl-L-valine-L-alanine-L-aspartic acid 5-(1-phenyl-3-trifluoromethyl) pyrazolyloxymethyl ketone. Mass spectrum: m/z= 662 (M+H)

EXAMPLE 13

N-Benzyloxycarbonyl-L-aspartic acid 5-(1-(m.p-dichlorophenyl)-3-methyl)pyrazolyloxymethyl ketone.

Mass spectrum: m/z=560 (M+)

EXAMPLE 14

N-Benzyloxycarbonyl-L-valine-L-aspartic acid 5-(1-phenyl-3-trifluoromethyl)-pyrazolyloxymethyl ketone.

Mass spectrum: m/z=591 (M+H)

EXAMPLE 15

N-Benzyloxycarbonyl-L-valine-L-aspartic acid 5-(1-phenyl-3-methyl)pyrazolyloxymethyl ketone.

Mass spectrum: m/z=537 (M+H)

EXAMPLE 16

N-Benzyloxycarbonyl-L-valine-L-aspartic acid 5-(1-phenyl-3-t-butyl)pyrazolyloxymethyl ketone.

Anal. Calcd. for $C_{31}H_{38}N_4O_7 \cdot CF_3CO_2H \cdot 1.5\ H_2O$: C, 55.07; H, 5.88; N, 7.78. Found: C, 55.13; H, 5.48; N, 7.54

EXAMPLE 17

N-Benzyloxycarbonyl-L-valine-L-aspartic acid 5-(1-(p-trifluoromethylphenyl)-3-methyl)pyrazolyloxymethyl ketone.

Mass spectrum: m/z=605 (M+H)

EXAMPLE 18

N-Benzyloxycarbonyl-L-aspartic acid 5-(1-(p-methanesulfonylphenyl)-3-trifluoromethyl)pyrazolyloxymethyl ketone.

Mass spectrum: m/z=570 (M+H)

EXAMPLE 19

N-4-(N,N-Dimethylaminomethyl)benzoyl-L-valine-L-alanine-L-aspartic acid 5-(1-phenyl-3-trifluoromethyl)pyrazolyloxymethyl ketone.

m.p. 82°–84° C.

Example 20

N-Benzyloxycarbonyl-L-aspartic acid 5-(1.3-dimethyl-4-phenyl)pyrazolyloxymethyl ketone.

Anal. Calcd. for $C_{24}H_{25}N_3O_6 \cdot 1.25\ CF_2CO_2H$: C, 53.58; H, 4.45; N, 7.07. Found: C, 53.57; H, 4.57; N, 6.85

Example 21

N-Benzyloxycarbonyl-L-valine-L-aspartic acid 5-(1-(p-methanesulfonylphenyl)-3-methyl)pyrazolyloxymethyl ketone.

Mass spectrum: m/z=615 (M+H)

EXAMPLE 22

N-Benzyloxycarbonyl-L-valine-L-aspartic acid 5-(1.3-dimethyl-4-phenyl)pyrazolyloxymethyl ketone.

Mass spectrum: m/z=551 (M+H)

EXAMPLE 23

N-Benzyloxycarbonyl-L-valine-L-aspartic acid 5-(1-phenyl-3-carbethoxy)pyrazolyloxymethyl ketone.

Mass spectrum: m/z=595 (M+H)

EXAMPLE 24

N-Benzyloxycarbonyl-L-valine-L-aspartic acid 5-(1.3-diphenyl) pyrazolyloxymethyl ketone.

Mass spectrum: m/z=599 (M+H)

EXAMPLE 25

N-Methyl-N-4-[pyridyl)methyl]carbamoyl-L-valine-L-alanine-L-aspartic acid 5-(1-phenyl-3-trifluoromethyl)pyrazolyloxymethyl ketone. Mass spectrum: m/z=676 (M+H)

EXAMPLE 26

N-[4-(Pyridyl)methyl]carbamoyl-L-valine-L-alanine-L-aspartic acid 5-(1-phenyl-3- trifluoromethyl) pyrazolyloxymethyl ketone. Mass spectrum: m/z=662 (M+H)

EXAMPLE 27

N-Benzyloxycarbonyl-L-valine-L-alanine-D-aspartic acid 5-(1-phenyl-3- trifluoromethyl) pyrazolyloxymethyl ketone.

Mass spectrum: m/z=608 (M+H)

EXAMPLE 28

N-Benzyloxycarbonyl-L-vatine-L-aspartic acid 5-(1-(p-chlorophenyl)-3-methyl-4-phenyl) pyrazolyloxymethyl ketone.

Anal. Calcd. for $C_{34}H_{35}ClN_4O_7 \cdot 0.7\ CF3CO2H$: C, 58.49; H, 4.95; N, 7.71. Found: C, 58.68; H, 5.15; N, 7.34

EXAMPLE 29

N-Benzyloxycarbonyl-L-valine-L-aspartic acid 5-(1.4-diphenyl-3-methyl)pyrazolyloxymethyl ketone. Mass spectrum: m/z= 61 3 (M+H)

Example 30

N-3-(piperidinopropionyl)-L-valine-L-alanine-L-aspartic acid 5-(1-phenyl-3-methyl) pyrazolyloxymethyl ketone.

Mass spectrum: m/z=667 (M+H)

EXAMPLE 31

N-[4-(morpholinoethoxy)benzoyl]-L-valine-L-alanine-L-aspartic acid 5-(1-phenyl-3-trifluoromethyl)pyrazolyloxymethyl ketone.

Mass spectrum: m/z=761 (M+H)

EXAMPLE 32

N-2-(quinuclidinyl)carbonyl-L-valine-L-alanine-L-aspartic acid 5-(1-phenyl-3-trifluoromethyl) pyrazolyloxymethyl ketone.

Mass spectrum: m/z=665 (M+H)

EXAMPLE 33

N-(3-pyridyl)methoxycarbonyl-L-valine-L-alanine-L-aspartic acid 5-(1-phenyl-3-trifluoromethyl) pyrazolyloxymethyl ketone.

Mass spectrum: m/z=663 (M+H)

EXAMPLE 34

N-(2-pyridyl)methoxycarbonyl-L-valine-L-alanine-L-aspartic acid 5-(1-phenyl-3-trifluoromethyl) pyrazolyloxymethyl ketone.

Mass spectrum: m/z=663 (M+H)

EXAMPLE 35

N-Methyl-N-benzylcarbamoyl-L-valine-L-alanine-L-aspartic acid 5-(1-phenyl-3-trifluoromethyl) pyrazolyloxymethyl ketone.

Mass spectrum: m/z=674 (M+H)

EXAMPLE 36

N-Methyl-N-[2-(4-pyridyl)ethyl]carbamoyl-L-valine-L-alanine-L-aspartic acid 5-(1-phenyl-3-trifluoromethyl)pyrazolyloxymethyl ketone.

Mass spectrum: m/z=690 (M+H)

EXAMPLE 37

N-(N-Phenylpiperazino)carbonyl-L-valine-L-alanine-L-aspartic acid 5-(1-phenyl-3-trifluoromethyl)pyrazolyloxy methyl ketone.

Mass spectrum: m/z=716 (M+H)

Compounds of the present invention were tested for IL-1β protease inhibition activity according to the following protocol:

Partially purified IL-1 β protease is stored at −80° C., thawed on ice, and preincubated for 10 minutes at 37° C. with 2.5 mM dithiothreitol in a buffer solution containing 10 mM Tris-HCl (pH 8.0) and 25% (v/w) glycerol. Inhibitors are prepared as stock solutions in dimethyl sulfoxide (DMSO). The protease is preincubated with inhibitor in a volume of 20 μL in a 1.5 mL polypropylene microcentrifuge tube for 15 minutes at 37° C. The volume of compound added to the assay is adjusted to yield a DMSO concentration in the preincubation of <15% (v/v). The enzyme assay is then initiated by the addition of substrate (TRITC-AYVHDAPVRS-NH$_2$) to yield a final concentration of 67 μM in a final volume of 30 μL. The reaction are carried out for 60 minutes at 37° C. in the dark and are terminated by the addition of 10 mL of 10% trifluoroacetic acid (TFA). Following the addition of 115 μL of 0.1% TFA, the samples are analyzed by high pressure liquid chromatography using a reverse phase (C18) column and elution with an acetonitrile/water/TFA gradient. Substrate and product are monitored by their absorbance at 550 nm and elute at 4.2 and 5.2 minutes, respectively.

The compounds of Example 1–37 possess IL-1β protease inhibition activity (IC$_{50}$) of <10 μm.

What is claimed is:

1. A compound of the formula for inhibiting interleukin-12β preotease activity:

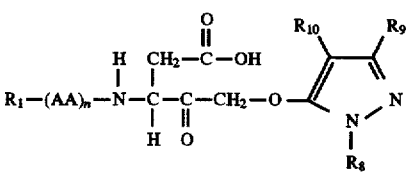

or a pharmaceutically acceptable salt thereof, wherein n is 0–2;

AA is independently L-valine or L-alanine;

R$_1$ is selected from the group consisting of

N-[4-(N,N-dimethylaminomethyl)] benzoyl,

N-benzyloxycarbonyl,

N-methyl-N- [4- (pyridyl)methyl],

N-[4-(pyridyl)methyl] carbonyl,

N-3-(piperidinopropionyl),

N-[4-(morpholinoethoxy) benzoyl,

N-2-(quinuclidinyl) carbonyl,

N-(3-pyridyl)methoxy carbonyl,

N-(2-pyridyl)methoxy carbonyl,

N-methyl-N-benzyl carbonyl,

N-methyl-N-[2-(4-pyridyl)ethyl] carbonyl, and

N-(N-phenylpiperazino) carbonyl;

R$_8$, R$_9$ and R$_{10}$ are each independently alkenyl, aryl, heteroaryl, aralkyl, heteroaralkyl, aralkenyl, heteroaralkenyl, hydroxy, alkoxy, 2-(alkyoxy)ethoxy, 2-(alkyoxy)aminoethyl and 2-(alkyoxy)-N-alkylaminoethyl, aralkoxy, heteroaralkoxy, alkylacyloxy, aralkylacyloxy, heteroaralkylacyloxy, aracyloxy, heteroaracyloxy, aryloxyalkylacyloxy, heteroaryloxyalkylacyloxy, alkylacyl, aralkylacyl, heteroaralkylacyl, alkylacylamino, aralkylacylamino, heteroaralkylacylamino, aracylamino, heteroaracylamino, aryloxyalkylacylamino, heteroaryloxyalkylacylamino, alkyloxyalkylacylamino, alkoxyacylamino, aralkoxyacylamino, heteroaralkoxyacylamino, aracyl, heteroaracyl, aryloxyalkylacyl, heteroaryloxyalkylacyl, halo, haloalkyl, guanidino, mono- and di-alkylguanidino, mono- and di-aralkylguanidino, mono- and di-heteroaralkylguanidino, alkylacylguanidino, aralkylacylguanidino, heteroaralkylguanidino, aracylguanidino, heteroarylguanidino, amidino, mono- and di-alkylamidino, mono- and diaralkylamidino, mono- and di-heteroaralkylamidino, amino, mono- and dialkylamino, mono- and di-aralkylamino, mono- and di-heteroaralkylamino, carboxy, alkylcarboxy, carbalkoxy, carbheteroaralkoxy, carbalkoxyalkenyl, carboxamido, mono- and dialkylcarboxamido, mono- and diarcarboxamido, mono and di-heteroarcarboxamido, mono- and di-aralkylcarboxamido, mono- and di-heteroaralkylcarboxamido, thio, alkylthio, arylthio, heteroarylthio, aralkylthio, heteroaralkylthio, sulfonamido, mono- and di-alkylsulfonamido, mono- and di-aralkylsulfonamido, mono- and di-heteroaralkylsulfonamido, morpholinosulfonamido, alkylsulfonyl, aralkylsulfonyl, heteroaralkylsulfonyl, arylsulfonyl, heteroarylsulfonyl, nitro, cyano, N-morpholinoalkyl, N-morpholinoalkoxy, N-morpholinoaralkyl, N-morpholinoaralkoxy, N-morpholinoheteroaralkyl, N-morpholinoheteroaralkoxy, N-mono and N,N-dialkylaminoalkyl and N-mono- and N,N-dialkylaminoethoxy, quinuclidinylamino, quinuclidinyloxy, quinuclidinocarbonyl or ureido; and where $R_9$ and $R_{10}$ are taken together may be heteroaryl, cyclopentyl, cyclohexyl, cycloheptyl or cyclooctyl.

2. A pharmaceutical composition for inhibiting interleukin-1β protease activity comprising an effective inhibitory amount of a compound of the formula:

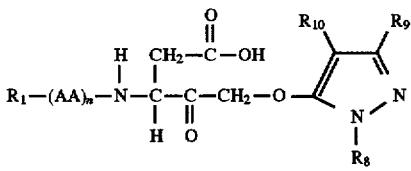

or a pharmaceutically acceptable salt thereof, wherein n is 0–2;

AA is independently L-valine or L-alanine;

$R_1$ is selected from the group consisting of
N-[4-(N,N-dimethylaminomethyl)] benzoyl,
N-benzyloxycarbonyl,
N-methyl-N- [4-(pyridyl)methyl],
N-[4-(pyridyl)methyl] carbonyl,
N-3-(,piperidinopropionyl),
N-[4-(morpholinoethoxy) benzoyl,
N-2-(quinuclidinyl) carbonyl,
N-(3-pyridyl)methoxy carbonyl,
N-(2-pyridyl)methoxy carbonyl,
N-methyl-N-benzyl carbonyl,
N-methyl-N-[2-(4-pyridyl)ethyl] carbonyl, and
N-(N-phenylpiperazino) carbonyl;

$R_8$, $R_9$ and $R_{10}$ are each independently alkenyl, aryl, heteroaryl, aralkyl, heteroaralkyl, aralkenyl, heteroaralkenyl, hydroxy, alkoxy, 2-(alkyoxy)ethoxy, 2-(alkyoxy)aminoethyl and 2-(alkyoxy)-N-alkylaminoethyl, aralkoxy, heteroaralkoxy, alkylacyloxy, aralkylacyloxy, heteroaralkylacyloxy, aracyloxy, heteroaracyloxy, aryloxyalkylacyloxy, heteroaryloxyalkylacyloxy, alkylacyl, aralkylacyl, heteroaralkylacyl, alkylacylamino, aralkylacylamino, heteroaralkylacylamino, aracylamino, heteroaracylamino, aryloxyalkylacylamino, heteroaryloxyalkylacylamino, alkyloxyalkylacylamino, alkoxyacylamino, aralkoxyacylamino, heteroaralkoxyacylamino, aracyl, heteroaracyl, aryloxyalkylacyl, heteroaryloxyalkylacyl, halo, haloalkyl, guanidino, mono- and di-alkylguanidino, mono- and di-aralkylguanidino, mono- and di-heteroaralkylguanidino, alkylacylguanidino, aralkylacylguanidino, heteroaralkylguanidino, aracylguanidino, heteroarylguanidino, amidino, mono- and di-alkylamidino, mono- and diaralkylamidino, mono- and di-heteroaralkylamidino, amino, mono- and dialkylamino, mono- and di-aralkylamino, mono- and di-heteroaralkylamino, carboxy, alkylcarboxy, carbalkoxy, carbheteroaralkoxy, carbalkoxyalkenyl, carboxamido, mono- and dialkylcarboxamido, mono- and diarcarboxamido, mono and di-heteroarcarboxamido, mono- and di-aralkylcarboxamido, mono- and di-heteroaralkylcarboxamido, thio, alkylthio, arylthio, heteroarylthio, aralkylthio, heteroaralkylthio, sulfonamido, mono- and di-alkylsulfonamido, mono- and di-aralkylsulfonamido, mono- and di-heteroaralkylsulfonamido, morpholinosulfonamido, alkylsulfonyl, aralkylsulfonyl, heteroaralkylsulfonyl, arylsulfonyl, heteroarylsulfonyl, nitro, cyano, N-morpholinoalkyl, N-morpholinoalkoxy, N-morpholinoaralkyl, N-morpholinoaralkoxy, N-morpholinoheteroaralkyl, N-morpholinoheteroaralkoxy, N-mono and N,N-dialkylaminoalkyl and N-mono- and N,N-dialkylaminoethoxy, quinuclidinylamino, quinuclidinyloxy, quinuclidinocarbonyl or ureido;

and where $R_9$ and $R_{10}$ are taken together may be heteroaryl, cyclopentyl, cyclohexyl, cycloheptyl or cyclooctyl.

3. A method for inhibiting interleukin-1β protease activity in a mammal in need of such treatment comprising administering to said mammal an effective interleukin-1β protease inhibitory amount of a pharmaceutical composition comprising a compound of the formula:

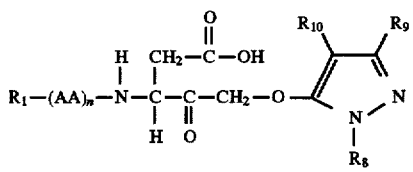

or a pharmaceutically acceptable salt thereof, wherein n is 0–2;

AA is independently L-valine or L-alanine;

$R_1$ is selected from the group consisting of
N-[4-(N,N-dimethylaminomethyl)] benzoyl,
N-benzyloxycarbonyl,
N-methyl-N-[4-(pyridyl)methyl],
N-[4-(pyridyl)methyl] carbonyl,
N-3-(piperidinopropionyl),
N-[4-(morpholinoethoxy) benzoyl,
N-2-(quinuclidinyl) carbonyl,
N-(3-pyridyl)methoxy carbonyl,
N-(2-pyridyl)methoxy carbonyl,
N-methyl-N-benzyl carbonyl,
N-methyl-N-[2-(4-pyridyl)ethyl] carbonyl, and
N-(N-phenylpiperazino) carbonyl;

$R_8$, $R_9$ and $R_{10}$ are each independently alkenyl, aryl, heteroaryl, aralkyl, heteroaralkyl, aralkenyl, heteroaralkenyl, hydroxy, alkoxy, 2-(alkyoxy)ethoxy, 2-(alkyoxy)aminoethyl and 2-(alkyoxy)-N-alkylaminoethyl, aralkoxy, heteroaralkoxy, alkylacyloxy, aralkylacyloxy, heteroaralkylacyloxy, aracyloxy, heteroaracyloxy, aryloxyalkylacyloxy, heteroaryloxyalkylacyloxy, alkylacyl, aralkylacyl, heteroaralkylacyl, alkylacylamino, aralkylacylamino, heteroaralkylacylamino, aracylamino, heteroaracylamino, aryloxyalkylacylamino, heteroaryloxyalkylacylamino, alkyloxyalkylacylamino, alkoxyacylamino, aralkoxyacylamino, heteroaralkoxyacylamino, aracyl, heteroaracyl, aryloxyalkylacyl, heteroaryloxyalkylacyl, halo, haloalkyl, guanidino, mono- and di-alkylguanidino, mono- and di-aralkylguanidino, mono- and di-heteroaralkylguanidino, alkylacylguanidino, aralkylacylguanidino, heteroaralkylguanidino, aracylguanidino, heteroarylguanidino, amidino, mono- and di-alkylamidino, mono- and diaralkylamidino, mono- and di-heteroaralkylamidino, amino, mono- and dialkylamino, mono- and di-aralkylamino, mono- and di-heteroaralkylamino, carboxy, alkylcarboxy, carbalkoxy, carbheteroaralkoxy, carbalkoxyalkenyl, carboxamido, mono- and dialkylcarboxamido, mono- and diarcarboxamido, mono and di-heteroarcarboxamido, mono- and di-aralkylcarboxamido, mono- and di-heteroaralkylcarboxamido, thio, alkylthio, arylthio, heteroarylthio, aralkylthio, heteroaralkylthio, sulfonamido, mono- and di-alkylsulfonamido, mono- and di-aralkylsulfonamido, mono- and di-heteroaralkylsulfonamido, morpholinosulfonamido, alkylsulfonyl, aralkylsulfonyl, heteroaralkylsulfonyl, arylsulfonyl, heteroarylsulfonyl, nitro, cyano, N-morpholinoalkyl, N-morpholinoalkoxy, N-morpholinoaralkyl, N-morpholinoaralkoxy, N-morpholinoheteroaralkyl, N-morpholinoheteroaralkoxy, N-mono and N,N-dialkylaminoalkyl and N-mono- and N,N-dialkylaminoethoxy, quinuclidinylamino, quinuclidinyloxy, quinuclidinocarbonyl or ureido;

and where $R_9$ and $R_{10}$ are taken together may be heteroaryl, cyclopentyl, cyclohexyl, cycloheptyl or cyclooctyl.

* * * * *